(12) United States Patent
Anderson

(10) Patent No.: US 10,463,467 B2
(45) Date of Patent: *Nov. 5, 2019

(54) DUAL END BELLOW PROSTHESIS INSERTION DEVICE

(71) Applicant: Robert G Anderson, Aledo, TX (US)

(72) Inventor: Robert G Anderson, Aledo, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/117,696

(22) Filed: Aug. 30, 2018

(65) Prior Publication Data

US 2018/0368963 A1 Dec. 27, 2018

Related U.S. Application Data

(63) Continuation of application No. 15/661,427, filed on Jul. 27, 2017, now Pat. No. 10,092,385, which is a
(Continued)

(51) Int. Cl.
*A61F 2/00* (2006.01)
*A61B 17/02* (2006.01)
(Continued)

(52) U.S. Cl.
CPC ............ *A61F 2/0095* (2013.01); *A61B 17/02* (2013.01); *A61F 2/12* (2013.01);
(Continued)

(58) Field of Classification Search
CPC .... A61F 2/12; A61F 2250/0003; A61L 27/18; A61L 2430/04; C08L 83/04
(Continued)

(56) References Cited

U.S. PATENT DOCUMENTS 4,641,648 A 2/1987 Shapiro
4,995,906 A 2/1991 Iwasaki et al.
(Continued)

FOREIGN PATENT DOCUMENTS

CA 2861438 A1 8/2013
WO 2013122568 A1 8/2013

OTHER PUBLICATIONS

Richard A. Mladick, M.D., F.A.C.S. "No-Touch" Submuscular Saline Breast Augmentation Technique, Aesthetic Plastic Surgery, 17:1 83-192, 1993, New York, NY.
(Continued)

*Primary Examiner* — Christopher D. Prone
*Assistant Examiner* — Tiffany P Shipmon
(74) *Attorney, Agent, or Firm* — Kirby Drake

(57) ABSTRACT

An apparatus and method for inserting prosthesis implants into a patient pocket. The apparatus has three openings including a prosthesis opening and two implant insertion openings. The apparatus prevents infection; eases insertion and placement; and reduces complications. In use, the first implant insertion end of the bellow is placed through the patient incision while allowing the bellow to be manipulated to force the first implant into a surgical pocket of a patient. Then the bellow is rotated 180 degrees so that the second implant insertion end becomes the opening through which the second implant is inserted into the second incision while allowing the bellow to be manipulated to force the second implant into a surgical pocket.

1 Claim, 11 Drawing Sheets

Related U.S. Application Data continuation-in-part of application No. 15/179,983, filed on Jun. 11, 2016, now Pat. No. 9,808,285.

(60) Provisional application No. 62/348,338, filed on Jun. 10, 2016.

(51) Int. Cl.
*A61F 2/12* (2006.01)
*A61B 17/00* (2006.01)

(52) U.S. Cl.
CPC ............... *A61B 2017/00792* (2013.01); *A61B 2017/00836* (2013.01); *A61B 2017/00862* (2013.01)

(58) Field of Classification Search
USPC ............................................................ 623/8
See application file for complete search history.

(56) References Cited

U.S. PATENT DOCUMENTS

| | | | |
|---|---|---|---|
| 5,199,795 A | 4/1993 | Russo et al. | |
| 5,571,178 A | 11/1996 | Ledergerber | |
| 5,723,006 A | 3/1998 | Ledergerber | |
| 5,782,913 A | 7/1998 | Schindler et al. | |
| 8,206,443 B2 | 6/2012 | Preissman | |
| 8,211,173 B2 | 7/2012 | Keller et al. | |
| 8,313,760 B2 | 11/2012 | Hunter | |
| 8,550,090 B2 | 10/2013 | Keller et al. | |
| 8,555,893 B2 | 10/2013 | Keller et al. | |
| 8,641,758 B1 | 2/2014 | Anderson | |
| D738,490 S | 9/2015 | Anderson | |
| 2007/0276484 A1 | 11/2007 | Abell et al. | |
| 2009/0204107 A1 | 8/2009 | Keller et al. | |
| 2010/0280610 A1 | 11/2010 | Preissman | |
| 2011/0035003 A1 | 2/2011 | Preissman | |
| 2011/0218624 A1 | 9/2011 | Preissman | |
| 2012/0185042 A1 | 7/2012 | Preissman | |
| 2012/0259414 A1 | 10/2012 | Preissman | |
| 2013/0073040 A1 | 3/2013 | Preissman | |
| 2014/0074235 A1 | 3/2014 | Keller et al. | |
| 2014/0074236 A1 | 3/2014 | Keller et al. | |
| 2014/0148901 A1 | 5/2014 | Anderson | |
| 2015/0028056 A1* | 1/2015 | Massis | A23G 3/28 222/107 |
| 2017/0181841 A1* | 6/2017 | Weinzweig | A61F 2/12 |

OTHER PUBLICATIONS

Richard A. Mladick, M.D., F.A.C.S. "Significance of Staphylococcus Epidermidis Causing Subclinical Infection," Plastic & Reconstructive Surgery, Apr. 15, 2005, vol. 115, Issue 5, pp. 1426-1427.
Richard A. Mladick, M.D., F.A.C.S.. "Prevention of Capsular Contracture," Plastic & Reconstructive Surgery, May 1999, vol. 103, Issue 6, pp. 1773-1774.
Thomas M. Biggs, M.D., "Prefilled Saline Breast Implants Offer Significant Advantages," Aesthetic Surgery Journal, Sep. 1999, vol. 19, No. 5424.
Mitchel H. Brown, M.D., M.Ed., "Cohesive Silicone Gel Breast Implants in Aesthetic and Reconstructive Breast Surgery," Plastic & Reconstructive Surgery, Sep. 1, 2005, vol. 116, Issue 3, pp. 768-779.
"International Search Report," for PCT Patent Application No. PCT/US17/16255, dated Jun. 28, 2017, 5 pages.
"Written Opinion of the International Search Authority," for PCT Patent Application No. PCT/US17/16255, dated Jun. 28, 2017, 9 pages.
Shaa'ista Ameen, "'No-Touch' Breast-Implant Insertion Device," University of Cape Town, Department of Human Biology, MSc (Med) Thesis, submitted Jan. 2016, 123 pages.

* cited by examiner

DUAL END BELLOW PROSTHESIS INSERTION DEVICE

CROSS REFERENCE TO RELATED APPLICATIONS

This application is a continuation of U.S. Non-Provisional patent application Ser. No. 15/661,427 filed on Jul. 27, 2017, entitled "Dual End Bellow Prosthesis Insertion Device," which is a continuation-in-part of U.S. Non-Provisional patent application Ser. No. 15/179,983 filed on Jun. 11, 2016, entitled "Asymmetrical Dual Proximal Insertion Bellow," which is a non-provisional and claims the benefit under 35 U.S.C. § 119(e) of U.S. Provisional Patent Application Ser. No. 62/348,338 filed on Jun. 10, 2016, entitled "Opposing Proximal Insertion Ends Implant Devices," both of which are incorporated by reference in their entirety.

FIELD OF THE DISCLOSURE

The present disclosure relates to an apparatus and method of safely inserting a prosthesis into a human body.

BACKGROUND

Breast implants are a manufactured prosthesis used in cosmetic and reconstructive surgery. A breast implant has an outer casing or membrane that is filled with a fluid such as saline or a gelatinous cohesive silicone. Currently only about thirty percent (30%) of breast implant procedures are performed with an insertion device. An insertion device improves both the sterility of the surgical procedure and the patient outcome. Without an insertion device, the surgeon makes the incision, creates a pocket for the implant, opens the incision with a retractor and then manually pushes the implant into the pocket.

Different than a silicone implant, a saline implant is inserted into the pocket in an empty configuration. Once placed in the pocket, the surgeon takes the additional step of filling the empty implant with a saline solution using a fill tube. The incision is made in one of four places: in the armpit, in the breast fold, in the navel, or around the areola. Except for the navel insertion, one incision is made for each implant. It is preferable that the incision be as short as possible. Shorter incisions are less unsightly. This goal of a shorter incision is easier to accomplish with a saline implant. A saline implant is relatively easy to insert through a short incision, as the implant is unfilled and therefore small as it passes through the incision. For these inflatable implants, the surgeon rolls up the implant like a cigar and pushes it through the incision and into the pocket. In contrast, silicone implants are prefilled by the manufacturer resulting in a more difficult and complication-susceptible operation. For these pre-filled implants, the procedure requires a longer incision length.

After the initial incisions, the surgeon dissects a path through the tissue to the desired destination of the implant. Once that path has been created, a pocket is created for the implant superficial or deep to the pectoralis major muscle. The pocket may be formed in one of two places under the breast: subglandular (between the breast tissue and pectoralis major muscle) or subpectoral (under the pectoralis major muscle). The subglandular position places the prosthesis directly behind the mammary gland and in front of the pectoralis major muscle. Subpectoral places the implant partially under the pectoralis major muscle. Due to the shape and position of the pectoralis major muscle, a portion of the implant is not covered by the muscle.

Secondary surgery is common for patients with breast implants. Patients with breast implants may require surgery to change the placement (from subglandular to subpectoral or vice versa), correct palpable folding of the implant, remove a ruptured implant, treat infection, bleeding, breast pain, contracted scar tissue forming around the implant and collections of fluid around the implant. These additional surgeries have risks due to anesthesia, infection and bleeding. The overall secondary operation complication rate is about 15-18% for silicone gel breast augmentation within 3 years of the initial operation and up to 36-42% by 10 years from the initial breast implant surgery. Many re-operations are related to implant rupture (leakage), bleeding or capsular contracture. The major cause of re-operation after breast augmentation surgery is capsular contracture caused by shrinkage or contracture of the sac or capsule the body naturally forms around the implant.

Cellulitis, a skin-based infection, occurs in 2%-4% of patients, with some surgeons reporting much higher rates, and is usually from the bacteria normally present on the skin. Symptoms of infection may include fever, pain, swelling and redness. To reduce infection, surgeons give a single dose of antibiotics before the surgery, and use an antibiotic solution in the wound before implant placement. The antibiotic solution may double as the lubrication to allow easier insertion of the implant into the pocket. However, surgeons can reduce the rate of capsular contracture and infection down further by preventing the implant from touching the patient's skin during the insertion of the breast implant.

The implant insertion devices heretofore known suffer from several disadvantages:
1. The surgeon uses a single insertion end of the device to insert both implants exposing the second incision to bacterial contamination from the insertion device end touching the skin of the initial (first) incision and delivering bacteria into the second incision resulting in cellulitis, infection and or capsular contraction;
2. Requires the surgeon to resize the insertion device mid-operation to match two different implant sizes;
3. The opening through which the implant is loaded into the device is large enough for the implant to inadvertently slip out of the device resulting in bacteria on the skin touching the implant; and
4. The high cost of current implant insertion devices encourages re-use despite the manufacturer recommendation not to do so.

SUMMARY

Embodiments of the present disclosure may provide a system and method to insert two prostheses into a patient with maximum sterility. The method allows the surgeon to use the same size or two different size implants with a single device where a different end of the device is used to insert a single implant.

Accordingly, besides the objects and advantages of the system for a breast implant insertion device described above, several objects and advantages of the present disclosure may provide:
a) means to further improve sterility by preventing the device end from touching the patient's skin and then being inserted into a second incision;
b) a device for a procedure using two different size implants;
c) a simplified insertion method;

d) means to reduce anesthesia time;
e) a device that secures the implant safely in the device such that it will not become dislodged;
f) a single device that can be used for all sizes of implants; and
g) an easier manipulation of the implant.

Further objects and advantages of the present disclosure will become apparent from a consideration of the drawings and the ensuing description of the drawings.

BRIEF DESCRIPTION OF THE DRAWINGS

For a more complete understanding of this disclosure, reference is now made to the following description, taken in conjunction with the accompanying drawings, in which.

Figure 1:
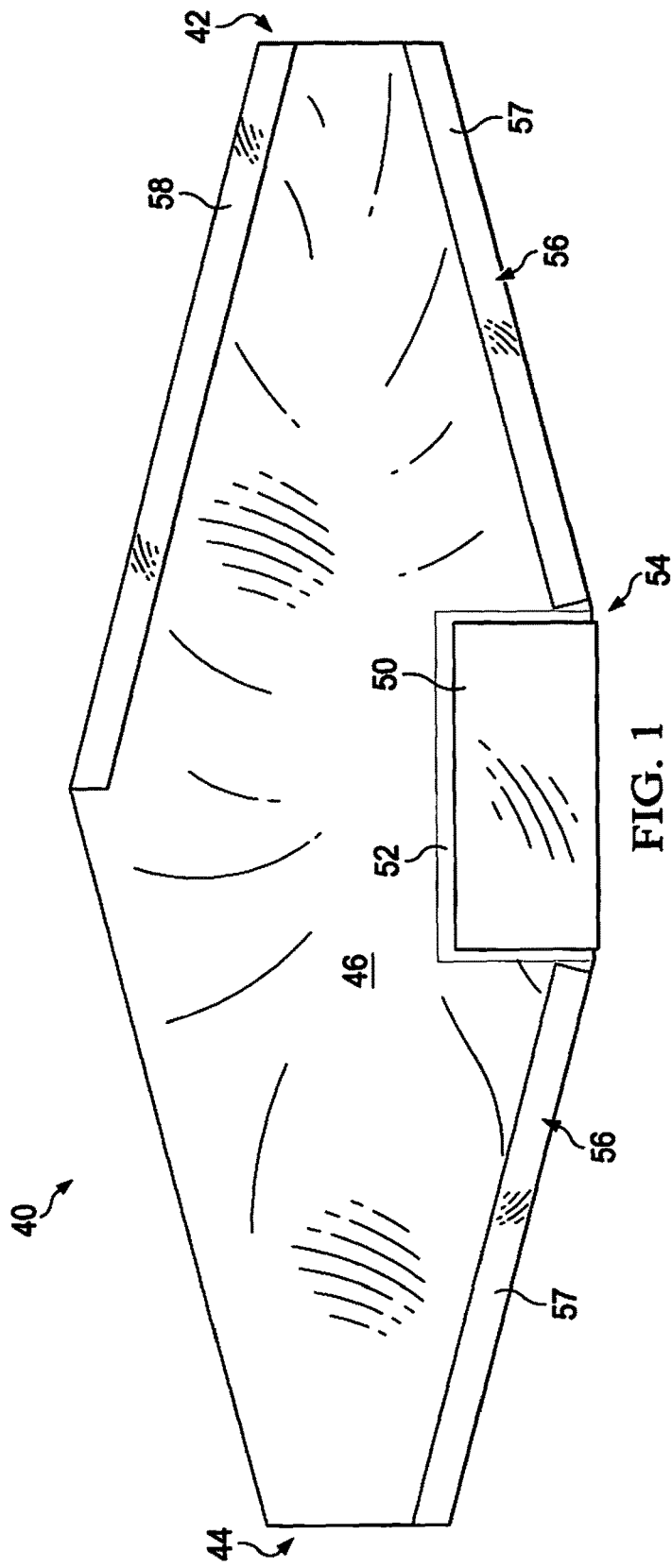
FIG. 1 depicts a top side perspective view of a bellow according to an embodiment of the present disclosure.

REFERENCE NUMERALS IN DRAWINGS 10 patient
20 patient's incision, opening
22 patient's breast
24 patient's implant pocket
25 patient's skin tissue
30 prosthesis, breast implant, implant
40 bellow
42 first insertion end
44 second insertion end
46 base fold
48 initial fold
50 exterior tab
52 internal tab
54 prosthesis opening
56 seal folds
57 tab-side seal tuck
58 abutted-side seal tuck
60 lubricant
70 retractor
72 retractor handle
74 retractor handle proximal end
76 retractor proximal end lip

DETAILED DESCRIPTION

Embodiments of the present disclosure may provide a dual end bellow prosthesis insertion device wherein each end may be trimmed as needed to accommodate breast implants that may be the same size or may be different sizes. It should be appreciated that the ends may have the same size opening in some embodiments of the present disclosure, but there may be other embodiments where one end is larger than the other end. There may be side flaps through which the implants may be inserted in the bellow, and these side flaps may be in the middle so that each implant may be placed in the bellow through a single opening, although only one implant may be loaded at a time. The implant may be inserted into the breast pocket, and the bellow may be turned around so that the second implant may be loaded into the bellow and inserted into the breast pocket through a second, unused end of the bellow. This may keep skin bacteria from being transferred from one implant pocket skin edge to the second implant pocket, which can occur if the two implants are inserted into the implant pockets using the same implant insertion device opening.

Referring now to FIG. 1, the top side perspective view of bellow 40 is manufactured with a sheet material such as plastic or a flexible, surgical-grade nylon. The plastic may be strengthened or reinforced with fibers. Bellow 40 may be clear, or semi-transparent, to allow observation of prosthesis 30 moving from bellow 40 into patient pocket 24.

Bellow 40 may have three openings: first insertion end 42 for inserting a range of implant sizes into incision 20; second insertion end 44 for insertion of a range of implant sizes into incision 20; and prosthesis opening 54, surrounded by exterior tab 50 and internal tab 52, for inserting prosthesis 30 into bellow 40. Each end 42, 44 may be considered an implant insertion end because bellow 40 is rotated during surgery so that each end 42, 44 is sequentially inserted in incision 20. FIG. 1 shows tabs 50, 52 located central to ends 42 and 44 and internal tab 52 pushed through prosthesis opening 54 to prevent the implant from passing to the outside of bellow 40, and exterior tab 50 folded over prosthesis opening 54. Exterior tab 50 may be folded and held in place by a surgeon's hands, friction or attached by glue, adhesive, heat bond, surgical tape or other coupling mechanism. While FIG. 1 shows both tabs 50, 52 folded into the working position, bellow exterior tab 50 and bellow internal tab 52 may initially be presented to the surgeon with both tabs 50, 52 outside of bellow 40 and surrounding prosthesis opening 54. While the preferred embodiment shows different sized tabs 50, 52 to distinguish exterior tab 50 from internal tab 52, tabs 50, 52 may be of the same size in embodiments of the present disclosure.

Bellow 40 may be assembled using seal tucks 56 which comprise two (2) tab-side seal tucks 57, and one (1) abutted-side seal tuck 58. In a preferred embodiment, the assembly may be done prior to packaging and shipping to the surgeon. In an alternate embodiment, seal tucks 56 may be sealed to base fold 46 by the patient's operating team. See FIG. 4B for additional illustration of the assembly using seal tucks 56.

Bellow 40 prevents breast implant 30 from touching the patient's skin tissue 28, prevents only one insertion end 42 or 44 from being used in both (right and left breast) incisions 20, and prevents damage to implant 30 during implant insertion. Bellow 40 may be manufactured to accommodate any breast implant 30 shape, volume, and diameter. Each insertion end 42, 44 may be trimmed by the surgeon to allow insertion of a range of implant 30 sizes. The manufacturer may also require or suggest two specific skin incision 20 lengths to allow insertion of the implant through bellow 40 into incision 20. The specifications take the burden off the surgeon to try to make shorter incisions 20.

Figure 2:
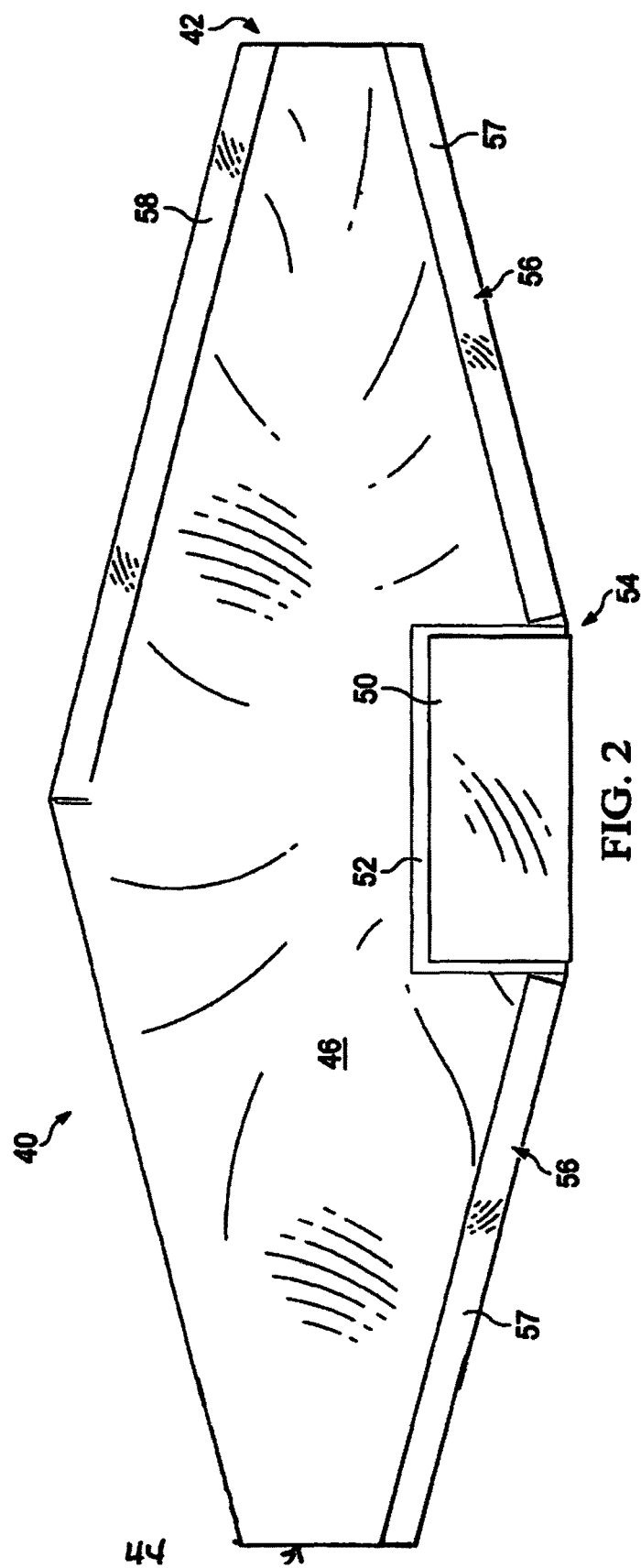
FIG. 2 depicts a bottom view of a bellow according to an embodiment of the present disclosure.

FIG. 2 shows a bottom view of the manufactured version of bellow 40 once bellow fold 48 is folded over base fold 46 along the abutted seam and three seal tucks 56 are adhered to base fold 46. Bellow 40 comprises initial fold 48 partially sealed on the periphery to base fold 46 so that it leaves implant insertion ends 42, 44, bellow prosthesis opening 54, bellow exterior tab 50 and bellow internal tab 52.

Figure 3:
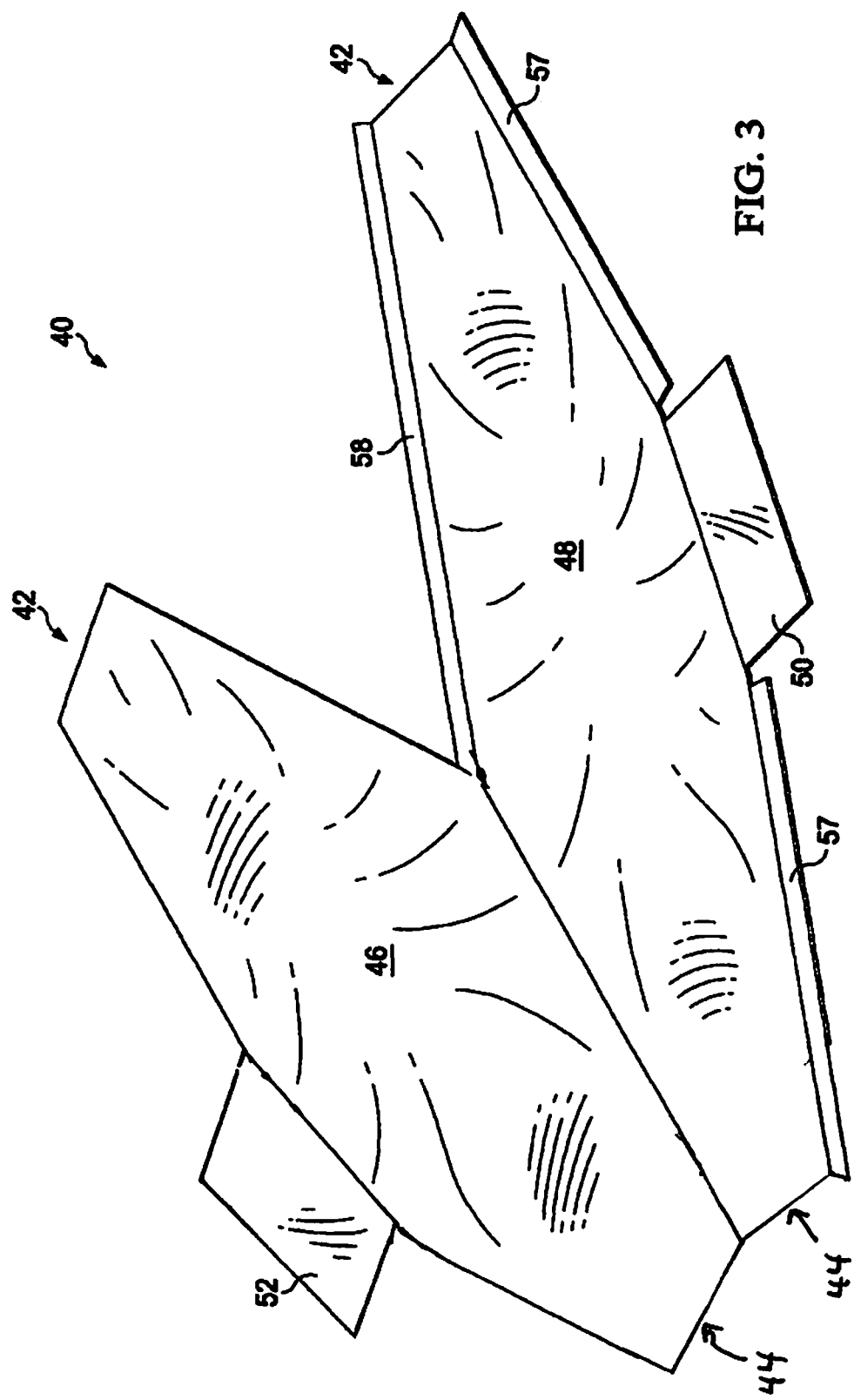
FIG. 3 depicts a top side view of an unassembled bellow according to an embodiment of the present disclosure.

Turning to FIG. 3, the illustration depicting a perspective view of unassembled bellow 40. Bellow 40 comprises two simple, convex, irregular hexagons folds 46, 48 with opposing prosthesis insertion tabs 50, 52. In a preferred embodiment, tabs 50, 52 are located centrally and opposing the abutted sides of manufactured bellow 40. In a preferred embodiment, as shown in FIGS. 3-4D, base fold 46 is manufactured abutted against initial fold 48 along either edge opposing the tabbed side of folds 46, 48. In a second embodiment, initial fold 48 and base fold 46 would be separately manufactured and assembled together at a later stage.

In the preferred embodiment, bellow 40 would be folded along an abutted edge and manufactured with three seal tucks 56 along: (a) initial fold 48 abutted-side edge from the abutment to second insertion end 44; (b) initial fold 48 tab-side edge from exterior tab 50 to first insertion end 42; and (c) initial fold 48 tab-side edge from exterior tab 50 to second insertion end 44.

In the second embodiment, bellow 40 would be manufactured with separated initial fold 48 and base fold 46, stacked over each other and assembled with four seal tucks 56 along: (a) initial fold 48 abutted-side edge from the abutment to first insertion end 42; (b) initial fold 48 abutted-side edge from the abutment to second insertion end 44; (c) initial fold 48 tab-side edge from exterior tab 50 to first insertion end 42; and (d) initial fold 48 tab-side edge from exterior tab 50 to second insertion end 44.

Bellow seal tucks 56 may be folded over opposing fold 46, 48 and attached by glue, adhesive, heat bond, surgical tape or other coupling mechanism.

In another embodiment, seal tucks 56 may be replaced with a simple seam along the edges to bind initial fold 48 and base fold 46 with glue, adhesive, heat bond, surgical tape or other coupling mechanism.

Figure 4A:
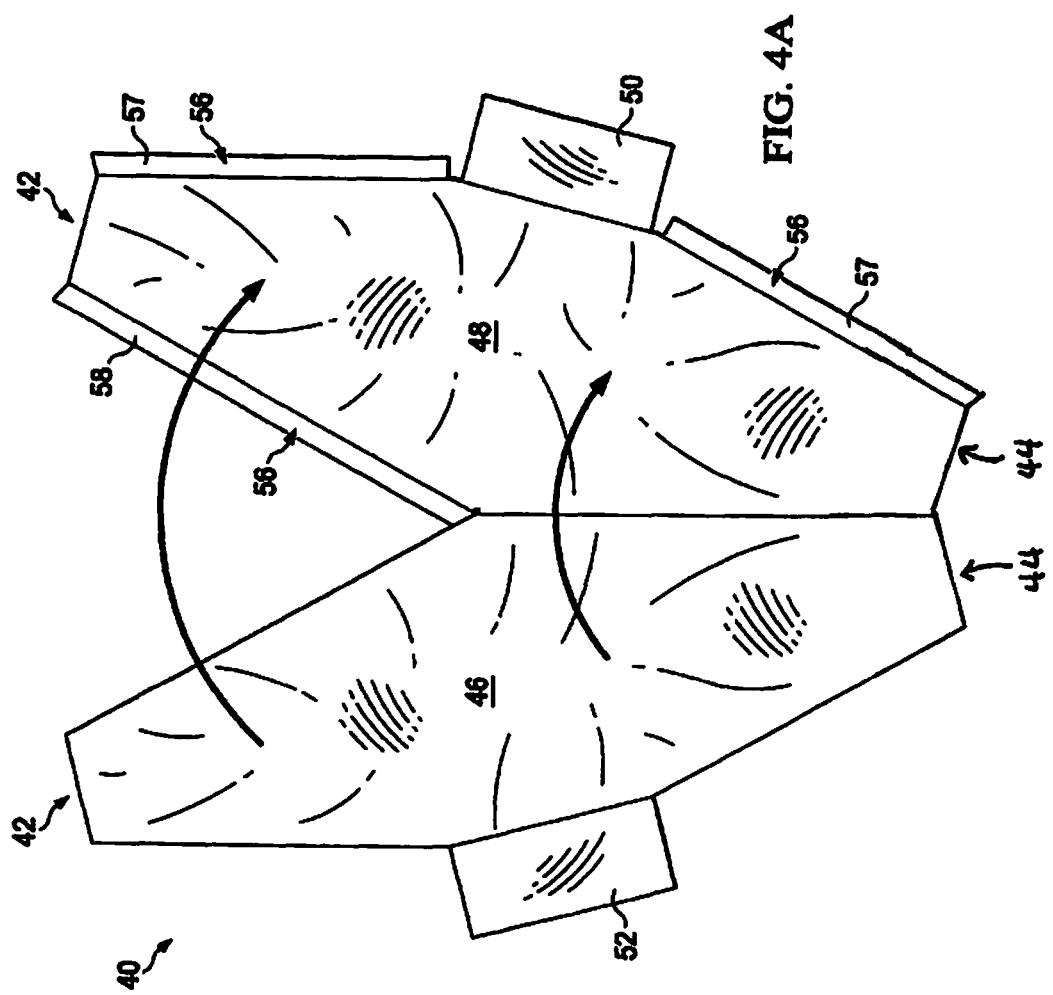
FIG. 4A depicts a top view of an unassembled bellow folded along the abutted edges according to an embodiment of the present disclosure.
Figure 4B:
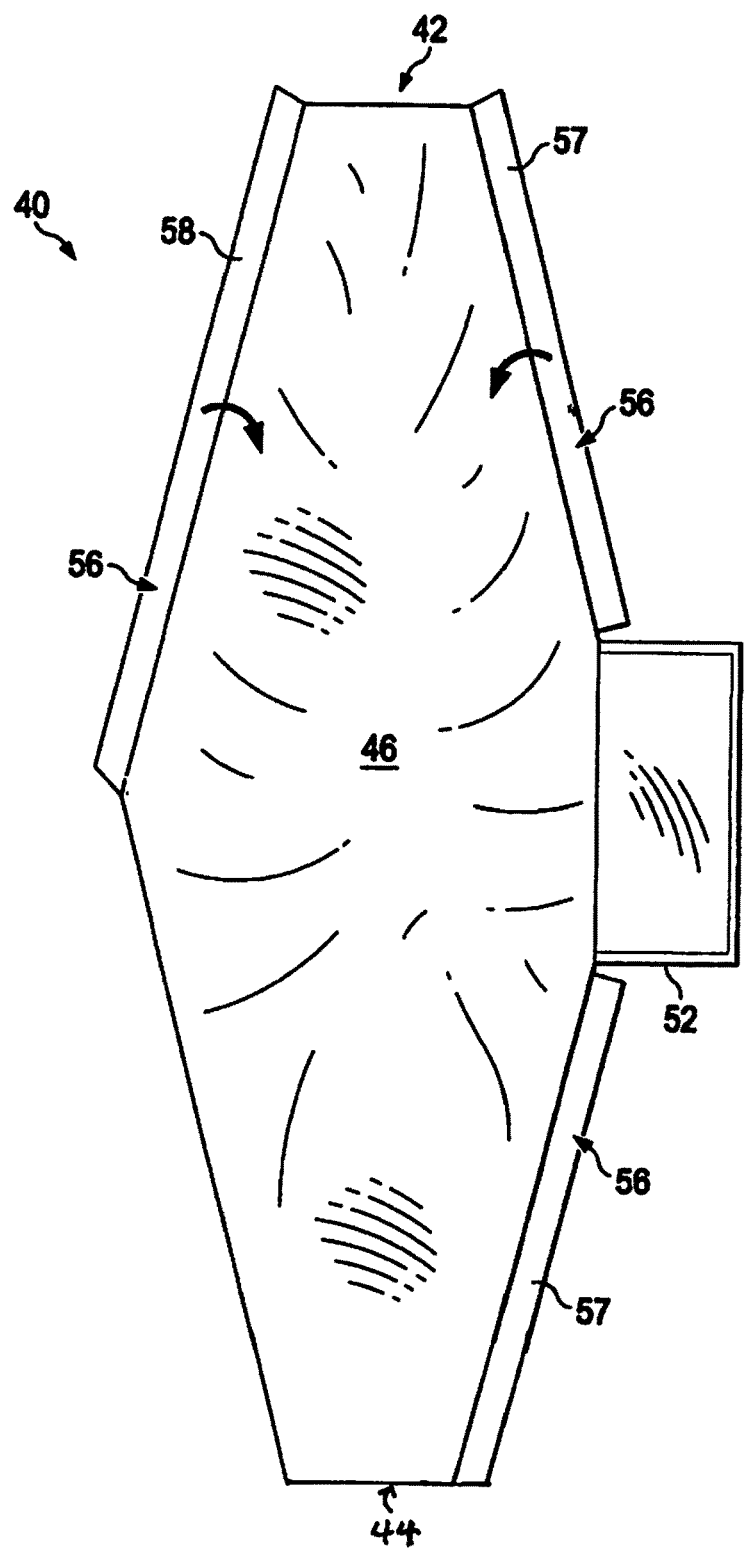
FIG. 4B depicts a top view of a bellow showing the base fold assembled over the initial fold according to an embodiment of the present disclosure.
Figure 4C:
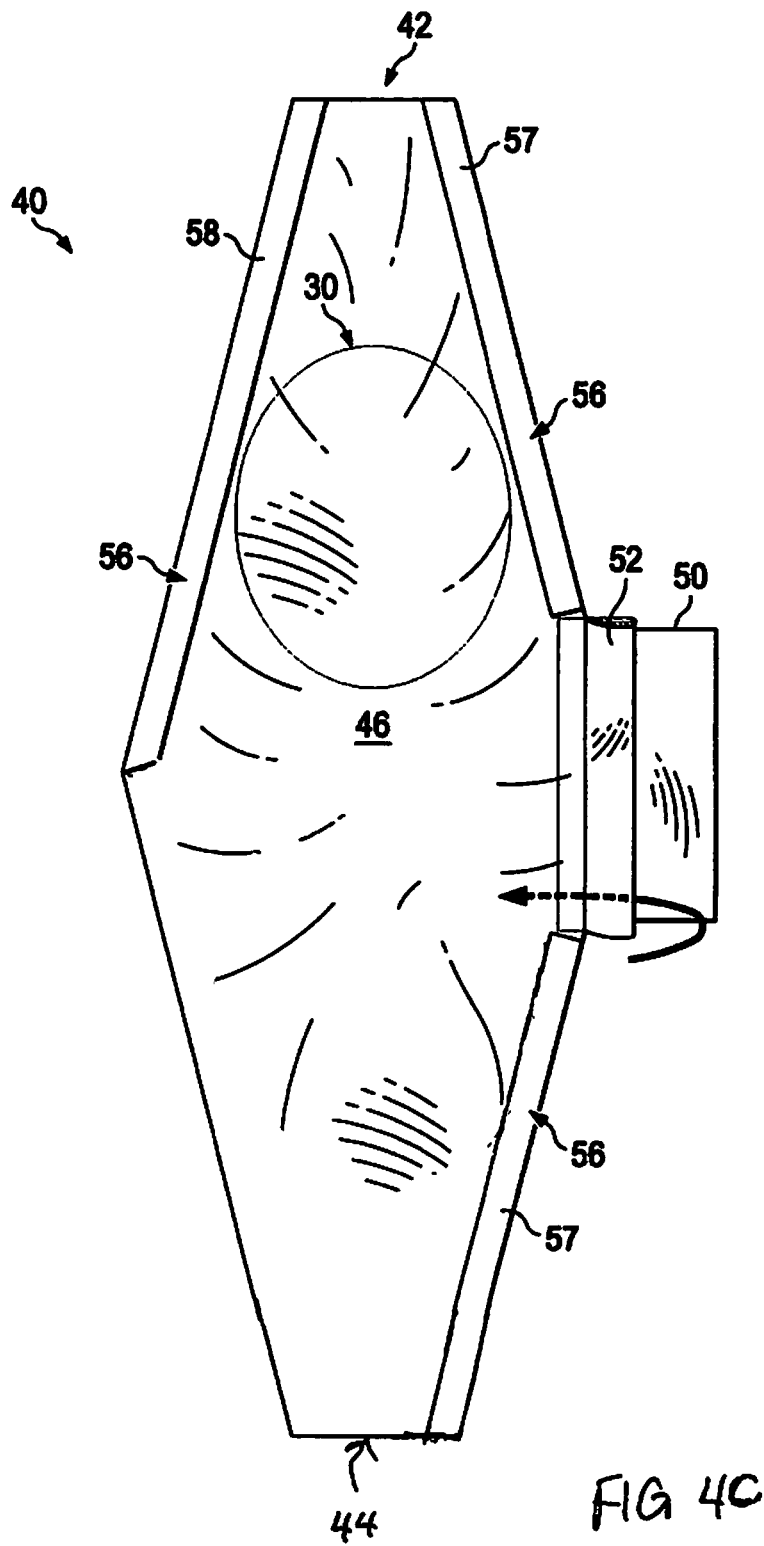
FIG. 4C depicts a top view of a bellow with the internal tab folded through prosthesis opening after the prostheses are inserted according to an embodiment of the present disclosure.
Figure 4D:
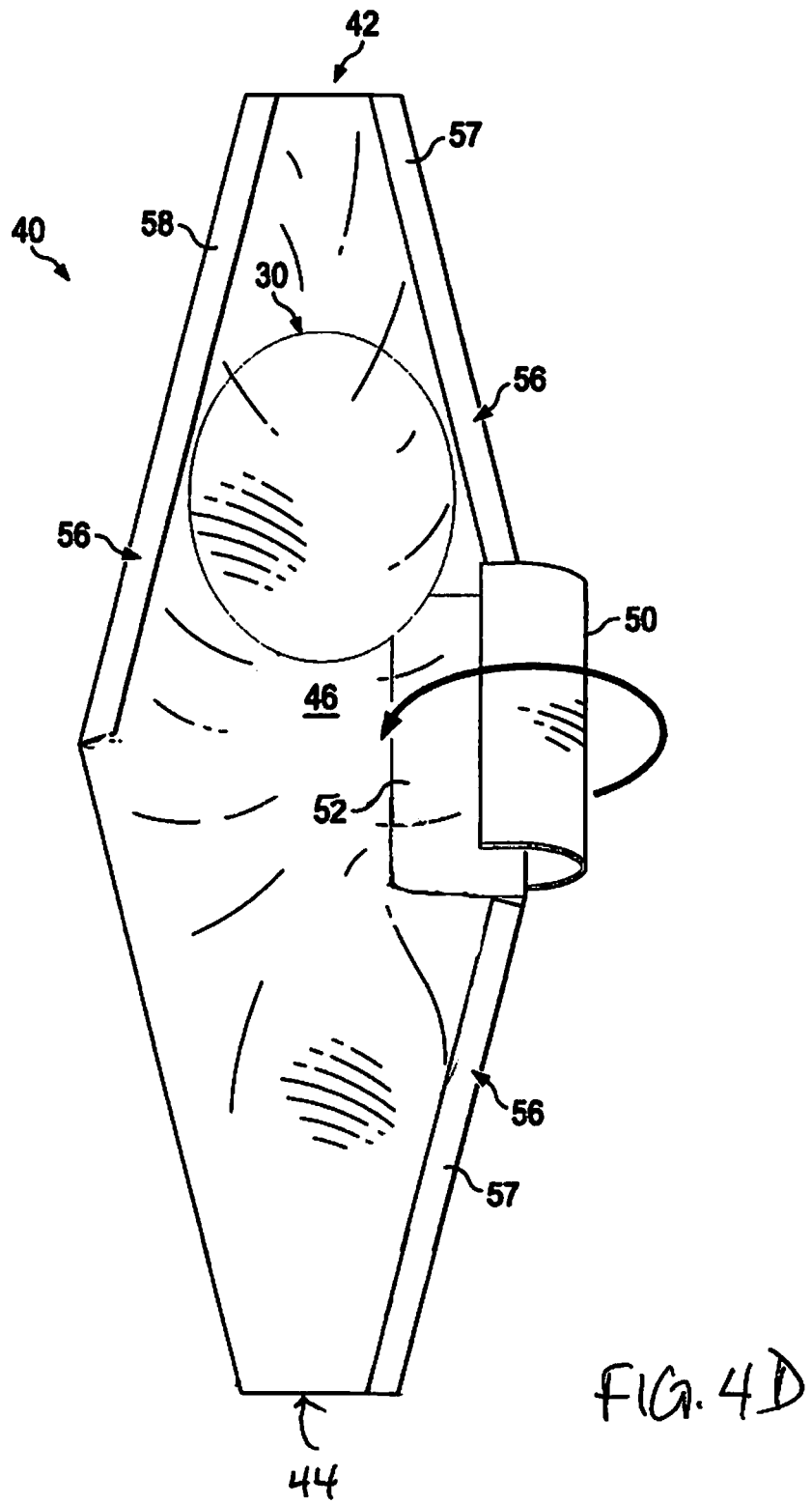
FIG. 4D depicts a top view of a bellow with the exterior tab being folded over the prosthesis opening according to an embodiment of the present disclosure.

FIGS. 4A to 4D show the assembly of bellow 40. In FIG. 4A, the pattern is folded along the abutted edge so that base fold 48 and initial fold 46 are stacked over each other with tabs 50, 52 pointing in the same direction.

Then in FIG. 4B, seal tucks 56 are folded over opposing fold 46, 48 and sealed to opposing fold 46, 48 with any desired manufacturing sealing technique.

With breast implant 30 in place inside bellow 40, FIG. 4C, internal tab 52 is pushed through prosthesis opening 54. Internal tab 52 prevents implant 30 from inadvertently ejecting through prosthesis opening 54 during the operation.

In FIG. 4D, with the internal tab 52 inside prosthesis opening 54, exterior tab 50 may be pushed over the top surface of opposing fold 46, 48. Exterior tab 50 may be secured to opposing fold 46, 48 with the surgeon's hands, surgical tape, heat seal, instant glue, or other forms of seals. Adhered seal 50 opposes prosthesis opening 54 and joins initial fold 48 and base fold 46.

Figure 5:
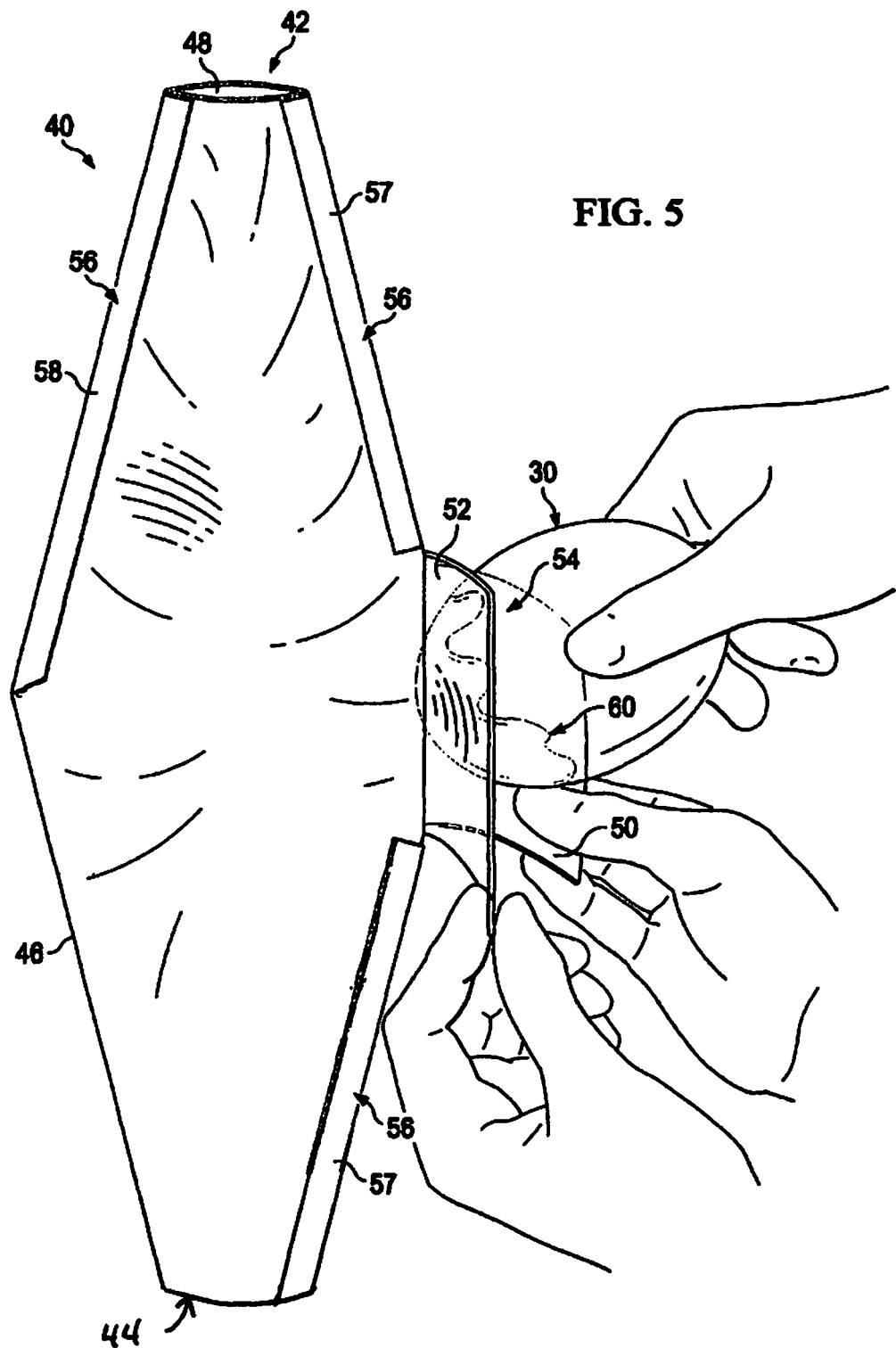
FIG. 5 depicts a front perspective view of a bellow with an implant being inserted through the prosthesis opening and into the device according to an embodiment of the present disclosure.

As illustrated in FIG. 5, in the preferred embodiment, a coating of surgical lubricant 60 may be used on implant 30 and the inner surface of bellow 40. As an alternative, bellow 40 may be provided with a coating that becomes slick when wet. In still another alternative, prosthesis 30 may be provided with a slick surface, such as surgical lubricant 80. The surgeon also has the option of applying lubricant 60 to prosthesis 30 directly before inserting into bellow 40. Lubricant 60 may also act as an antibiotic solution.

After lubrication, breast implant 30 is inserted into bellow 40 by the surgeon and nurse. To do so, the nurse opens bellow prosthesis opening 54 by separating tabs 50, 52, and the surgeon slides prosthesis 30 through bellow prosthesis opening 54. The surgeon would then fold internal tab 52 into bellow prosthesis opening 54 to prevent breast implant 30 from moving back out of opening 54. Exterior tab 50 may be left extended or folded over opposing fold 46, 48. If desired, exterior tab 50 may be sealed to opposing fold 46, 48. In a preferred embodiment, inserting prosthesis 30 into bellow 40 would be completed prior to inserting retractor 70 into patient incision 20. However, a surgeon could perform this step while bellow 40 is inserted in incision 20. In a preferred embodiment, the surgeon would insert one prosthesis 30 into bellow 40 at a time.

Figure 6:
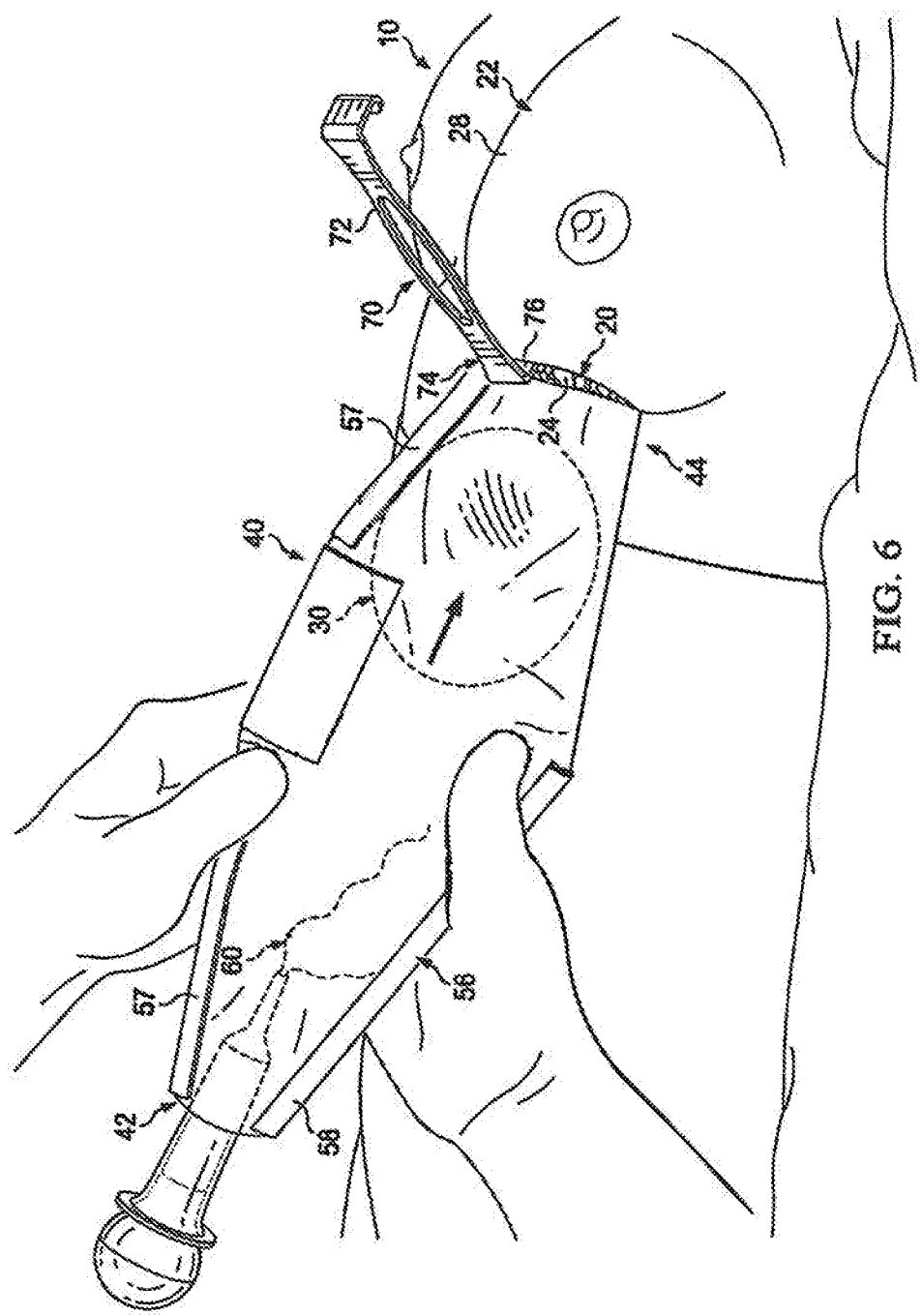
FIG. 6 depicts a side perspective view of the operating team adding lubricant to one end of the bellow according to an embodiment of the present disclosure.

In FIG. 6, the surgical team inserts lubricant 60 in opposing end 42, 44 of end 42, 44 inserted in incision 20. Liquid lubricant 60 surrounds breast implant 30 inside bellow 40. An antibiotic solution may be used as lubricant 60.

Figure 7A:
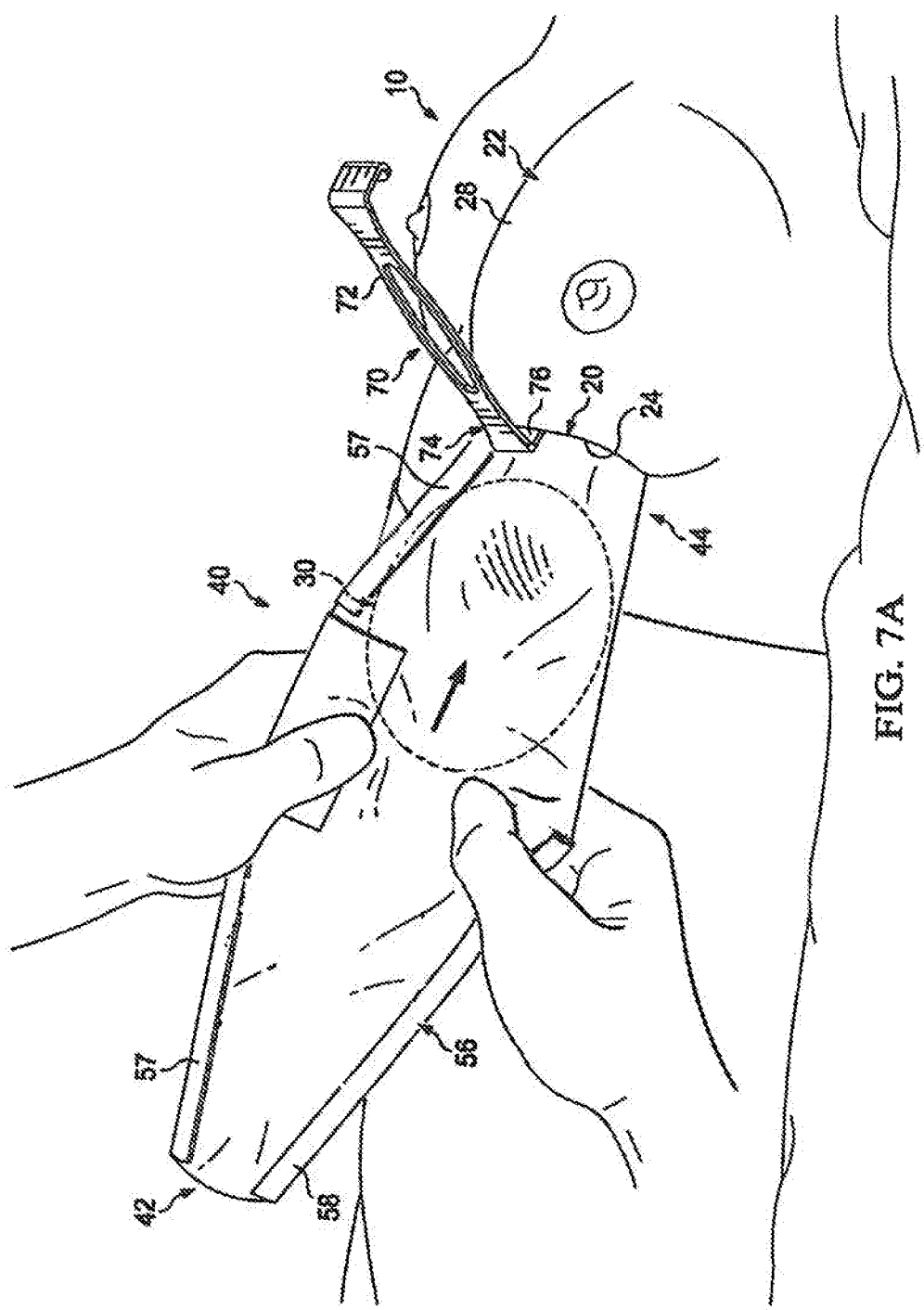
FIG. 7A depicts a left side perspective view of a bellow with first end inserted into the left patient incision according to an embodiment of the present disclosure.

FIG. 7A shows patient 10 positioned in a supine position prior to incision 20 being made in the patient's skin tissue 28. In the figure, incision 20 is cut in left-side inferior breast 22 crease. With incision 20 opened, the surgeon then forms pocket 24 in one of two places under breast 22: subglandular (between breast 22 tissue and pectoralis major muscle) or subpectoral (deep to the pectoralis major muscle). Pocket 24 is sized to match prosthesis 30. By manipulating retractor handle 72, retractor handle proximal end 74 and retractor proximal lip 76 are inserted into incision 20 to both retract incision 20 and hold incision 20 open.

Retractor 70 assembly comprises handle 72 located in the center, retractor handle proximal end 74, and retractor handle proximal end lip 76. Retractor 70 may have various shapes and sizes to match the application or surgeon preferences. Handle 72 of retractor 70 is bent or angled on the ends relative to the intermediate portion. Proximal end 74 of retractor 70 has lip 76 that is angled relative to end 74. Retractor 70 is made of metal, such as stainless steel, but may also be manufactured in a surgical plastic in other embodiments of the present disclosure.

Retractor proximal end 74 is structured and arranged to be inserted through incision 20 into pocket 24 of patient 10. Proximal end lip 76 helps maintain proximal end 74 of retractor 70 beneath skin tissue 28 of patient 10.

Retractor 70 extends laterally from bellow 40, so as not to interfere with the surgeon manipulating bellow 40, with the proximal ends of retractor 74 and proximal end lip 76 inserted into incision 20 and located under skin tissue 28 and moved to retract incision 20. Implant insertion ends 42, 44 of bellow 40 may be lubricated with lubricant 60 and inserted into open incision 20.

Bellow 40, distal to incision 20, is squeezed and/or twisted to force prosthesis 30 toward insertion end 42, 44 of bellow 40 and into pocket 24. Prosthesis 30 deforms to fit through second insertion end 44.

Once prosthesis 30 is located inside pocket 24, retractor 70 is removed from incision 20, followed by bellow 40. Incision 20 is then closed.

Figure 7B:
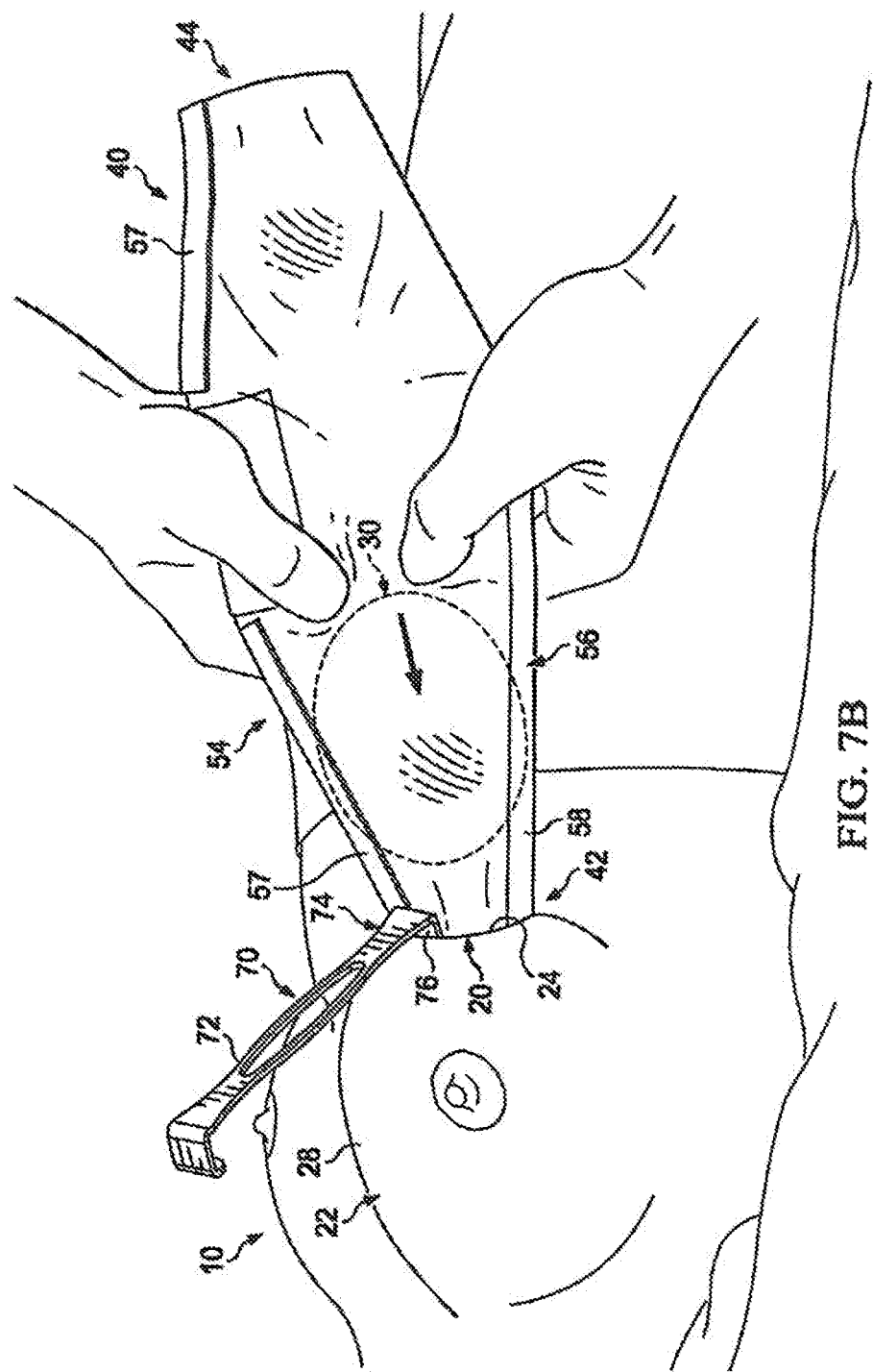
FIG. 7B depicts a rights side perspective view of a rotated bellow with the second end inserted into the right patient incision according to an embodiment of the present disclosure.

Finally, in FIG. 7B, showing a right-side of a patient, retractor 70 is inserted in second breast 22 incision 20 and moved to retract incision 20. Bellow 40 is then rotated so that the second unused implant insertion end 42 or 44 is introduced to incision 20 of second breast 22. The other implant insertion end 42 or 44 may be lubricated with lubricant 60 and inserted into open incision 20.

Bellow 40 is squeezed and/or twisted to force prosthesis 30 toward insertion end 42, 44 of bellow 40 and into pocket 24. Prosthesis 30 deforms to fit through insertion end 42,44.

Once prosthesis 30 is located inside pocket 24, retractor 70 is removed from second incision 20, followed by bellow 40. Second incision 20 is then closed.

If bellow 40 is designed for reuse, it is subjected to sterilization procedures. If bellow 40 is designed for single use, it is disposed of. One embodiment of bellow 40 and method is that implant insertion ends 42, 44 may be properly sized during manufacture with respect to each other so that smallest breast implants 30 will fit through first insertion end 42 and the larger range of implants 30 may be inserted through second insertion end 44. This allows the proper pressure to be applied to each range of implants 30 as they deform through insertion ends 42, 44.

Implant 30 is subject to damage if implant 30 is mishandled. Possible mishandling includes subjecting implant 30 to undue stresses or pressures, such as may be caused by attempting to squeeze implant 30 through implant insertion end 42, 44 that is too small, and folding of the external silastic shell, internal fracture of the cohesive silicone gel. A surgeon may make incision 20 in patient 10 that is too short for implant 30 and thus too much force is required to squeeze implant 30 into pocket 24. With bellow 40, implant 30 is protected from damage by the provision an adequate skin incision length and of the properly sized second insertion end 44. The major complication with implants 30 is capsular contracture thought to be due to sub-clinical infection. Sub-clinical infection is most likely caused by pushing implant 30 through skin incision 20, dragging natural skin 28 bacteria (still present after proper skin 28 preparations) into pocket 24 surgically created for implant 30. Use of bellow 40 prevents implant 30 from coming in contact with skin tissue 28 during the insertion process.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

In the foregoing description, and the following claims, method steps and/or actions are described in a particular order for the purposes of illustration. It should be appreciated that in alternate embodiments, the method steps and/or actions may be performed in a different order than that described. Additionally, the methods described above may be embodied in machine-executable instructions stored on one or more machine-readable mediums, such as disk drives, thumb drives or CD-ROMs. The instructions may be used to cause the machine (e.g., computer processor) programmed with the instructions to perform the method. Alternatively, the methods may be performed by a combination of hardware and software. While illustrative and presently preferred embodiments of the present disclosure have been described in detail herein, it is to be understood that the inventive concepts may be otherwise variously embodied and employed, and that the appended claims are intended to be construed to include such variations, except as limited by the prior art.

Benefits, other advantages, and solutions to problems have been described herein with regard to specific embodiments. However, the advantages, associated benefits, specific solutions to problems, and any element(s) that may cause any benefit, advantage, or solution to occur or become more pronounced are not to be construed as critical, required, or essential features or elements of any or all the claims of the present disclosure. As used herein, the terms "comprises", "comprising", or any other variation thereof, are intended to cover a non-exclusive inclusion, such that a process, method, article, or apparatus composed of a list of elements that may include other elements not expressly listed or inherent to such process, method, article, or apparatus.

From the description above, several advantages become evident for the dual end bellow prosthesis insertion device. Embodiments of the present disclosure may provide all new benefits for participating parties including manufacturers, patients and surgeons:

a) allow manufactures to ship a single breast implant insertion device for a pair of implants;
b) allows manufacturers to ship a single size bellow for all implant sizes;
c) allows patients a lower risk of complications;
d) allows physician to prevent contamination by skin bacteria, gross infection from using a single implant insertion end twice, resulting in infection and/or capsular contracture;
e) allows physician to eliminate damage to the implant during the insertion process;
f) allows physician a simplified insertion process;
g) speeds the implant insertion surgery.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. An apparatus for inserting a prosthesis through an incision into a surgical pocket, comprising:
   a bellow comprising two separate implant insertion ends that are configured to be sequentially inserted into the incision when the bellow is rotated during surgery, a prosthesis opening surrounded by folding tabs, a first tab-side seal tuck between the first separate implant insertion end and the prosthesis opening, a second tab-side seal tuck between the second separate implant insertion end and the prosthesis opening, and an abutted-side seal tuck opposite the prosthesis opening, the bellow being semi-rigid and structured and arranged to receive a breast implant through the prosthesis opening.

* * * * *